(12) United States Patent
Fritsch et al.

(10) Patent No.: US 9,675,595 B2
(45) Date of Patent: Jun. 13, 2017

(54) SYNERGISTIC COMBINATIONS OF PI3K- AND MEK-INHIBITORS

(75) Inventors: Christine Fritsch, Steinbach (FR); Xizhong Huang, Southborough, MA (US); Markus Boehm, Rheinfelden (DE); Emmanuelle di Tomaso, Lexington, MA (US); Jan Cosaert, Wommelgem (BE)

(73) Assignee: Novartis AG, Basel (CH)

( * ) Notice: Subject to any disclaimer, the term of this patent is extended or adjusted under 35 U.S.C. 154(b) by 22 days.

(21) Appl. No.: 14/240,499

(22) PCT Filed: Aug. 30, 2012

(86) PCT No.: PCT/US2012/052955
§ 371 (c)(1),
(2), (4) Date: Feb. 24, 2014

(87) PCT Pub. No.: WO2013/066483
PCT Pub. Date: May 10, 2013

(65) Prior Publication Data
US 2014/0179744 A1   Jun. 26, 2014

Related U.S. Application Data

(60) Provisional application No. 61/529,380, filed on Aug. 31, 2011, provisional application No. 61/542,463, filed on Oct. 3, 2011.

(51) Int. Cl.
| | |
|---|---|
| *A61K 31/44* | (2006.01) |
| *A61K 31/415* | (2006.01) |
| *A61K 31/4439* | (2006.01) |
| *A61K 45/06* | (2006.01) |
| *A61K 31/4184* | (2006.01) |
| *A61K 31/4412* | (2006.01) |

(52) U.S. Cl.
CPC ...... *A61K 31/4439* (2013.01); *A61K 31/4184* (2013.01); *A61K 31/4412* (2013.01); *A61K 45/06* (2013.01)

(58) Field of Classification Search
CPC ............... A61K 31/4439; A61K 45/06; A61K 31/4184; A61K 31/4412
USPC ........................................................ 514/342
See application file for complete search history.

(56) References Cited

U.S. PATENT DOCUMENTS

| | | | | |
|---|---|---|---|---|
| 7,777,050 B2* | 8/2010 | Wallace | ............... | C07D 235/06 548/304.7 |
| 8,227,462 B2* | 7/2012 | Fairhurst | ............... | C07D 417/14 514/235.8 |
| 2004/0116710 A1 | 6/2004 | Wallace | | |
| 2006/0014768 A1 | 1/2006 | Kawasaki | | |
| 2011/0086837 A1* | 4/2011 | Belvin | ............... | A61K 31/5377 514/210.18 |
| 2011/0105521 A1 | 5/2011 | Garcia-Echeverria | | |

FOREIGN PATENT DOCUMENTS

| | | | | |
|---|---|---|---|---|
| RU | 2192861 C1 | 6/2001 | | |
| WO | 03/077914 A1 | 9/2003 | | |
| WO | 2006/122806 A2 | 11/2006 | | |
| WO | 2007/030377 A1 | 3/2007 | | |
| WO | 2007/044084 A2 | 4/2007 | | |
| WO | 2007/084786 A1 | 7/2007 | | |
| WO | 2008/032162 A1 | 3/2008 | | |
| WO | 2010006225 A1 | 1/2010 | | |
| WO | 2010/029082 A1 | 3/2010 | | |
| WO | 2010029082 A1 | 3/2010 | | |
| WO | WO 2010/029082 A1 * | 3/2010 | ........... | C07D 417/14 |
| WO | 2011/054620 A1 | 5/2011 | | |
| WO | 2011054620 A1 | 5/2011 | | |

OTHER PUBLICATIONS

Engelman et al., "Effective use of PI3K and MEK inhibitors to treat mutant Kras G12D and PIK3CA H1047R murine lung cancers", 2008, Nature Medicine, vol. 14, No. 12, pp. 1351-1356.*
Hoeflich et al., "In vivo AntitumorActivity of MEK and Phosphatidylinositol 3-Kinase Inhibitors in Basal-Like Breast Cancer Models", 2009, Clin. Cancer Res., 15(14), pp. 4649-4664.*
Revill: "AZD-6244, MEK 1/2 Inhibitor Oncolytic", Drugs of the Future 2006, 31(10): 854-858.
Nishoka et al: "ZD6476 induces growth arrest and apoptosis of human leukemia cells, which is enhanced by concomitant use of a novel MEK inhibitor, AZD6244", Letters to the Editor, Lukemia 2007 21:1308-1310.
Shelton et al: "Ability of the activated PI3K/Akt oncoproteins to synergize with MEK1 and induce cell cylclle progression and abrogate the cytokine-dependence of hematopoietic cells", Cell Cycle 3:4, 503-512 Apr. 2004.
Chiu et al: "Actue activation of Erk1/Erk2 and protein kinase B/akt proceed by independent pathways in multiple cell types", The FEBS Journal 272 (2005) 4372-4384 2005.

(Continued)

*Primary Examiner* — My-Chau T Tran
(74) *Attorney, Agent, or Firm* — Sandra Rueck

(57) ABSTRACT

A pharmaceutical combination comprising (a) the phosphatidylinositol 3-kinase (PI3K) inhibitor compound (S)-pyrrolidine-1,2-dicarboxylic acid 2-amide 1-({4-methyl-5-[2-(2, 2,2-trifluoro-1,1-dimethyl-ethyl)-pyridin-4-yl]thiazol-2-yl}-amide) or a pharmaceutically acceptable salt thereof, and (b) at least one mitogen activated protein kinase (MEK) inhibitor or a pharmaceutically acceptable salt, and optionally at least one pharmaceutically acceptable carrier, for simultaneous, separate or sequential administration; the uses of such combination in the treatment of proliferative diseases; and methods of treating a subject suffering from a proliferative disease comprising administering a therapeutically effective amount of such combination.

2 Claims, 2 Drawing Sheets

(56) References Cited

OTHER PUBLICATIONS

Reference book "Antitumor chemotherapy" Second edition, revised and expanded, edited by Prof. Perevodchikova pp. 8-9 ,1993.
DACTOLISIB (CID 11977753) abstract [on-line] [found Apr. 2, 2013] (Found in PubChem; Create data Jan. 3, 2007).
RAF265 (CID 11656518) abstract [on-line] [found Apr. 2, 2013] (Found in PubChem; Create data Oct. 27, 2006).

* cited by examiner

SYNERGISTIC COMBINATIONS OF PI3K- AND MEK-INHIBITORS

RELATED APPLICATIONS

This application is a §371 filing based on International Application No. PCT/US2012/052955, filed Aug. 30, 2012, which claims the benefit of U.S. Provisional Patent Application Ser. No. 61/529,380, filed Aug. 31, 2011 and U.S. Provisional Patent Application Ser. No. 61/542,463, filed Oct. 3, 2011. The entire contents of these patent applications are hereby incorporated herein by reference.

FIELD OF THE INVENTION

A pharmaceutical combination comprising (a) a phosphatidylinositol 3-kinase (PI3K) inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, and (b) at least one mitogen activated protein kinase (MEK) inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier; the uses of such combination in the treatment or prevention of proliferative diseases, such as cancer; and methods of treating a subject suffering from a proliferative disease, such as cancer, comprising administering a therapeutically effective amount of such combination.

BACKGROUND OF THE INVENTION

Signaling through the mitogen-activated protein (MAP) kinase and phosphatidylinositol 3-kinases (PI3Ks)/AKT pathway is triggered by extracellular stimulation and regulates a variety of biological processes, such as proliferation, differentiation and cell death. Both pathways are often activated in many cancers by mutations or overexpression of upstream molecules. These pathways interact with each other to regulate tumor growth and, thus, they are potential targets in treating cancer.

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate (PIP2) and phosphoinositol-3,4,5-triphosphate (PIP3) that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., Annu. Rev. Biochem 70:535 (2001); Katso et al., Annu. Rev. Cell Dev. Biol. 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., Annu Rev. Biochem. 67:481 (1998); Suire et al., Curr. Biol. 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., Cell 89:105 (1997)); Katso et al., Annu. Rev. Cell Dev. Biol. 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., Cell 64:281 (1991); Escobedo and Williams, Nature 335:85 (1988); Fantl et al., Cell 69:413 (1992)).

PIP2 and PIP3 frequently recruit Akt, the product of the human homologue of the viral oncogene v-Akt, to the plasma membrane where it acts as a nodal point for many intracellular signaling pathways important for growth and survival (Fantl et al., Cell 69:413-423(1992); Bader et al., Nature Rev. Cancer 5:921 (2005); Vivanco and Sawyer, Nature Rev. Cancer 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers (Kang at el., Proc. Natl. Acad. Sci. USA 102:802 (2005); Samuels et al., Science 304:554 (2004); Samuels et al., Cancer Cell 7:561-573 (2005)). These observations show that deregulation of phosphoinositol-3 kinase and the upstream and downstream components of this signaling pathway is one of the most common deregulations associated with human cancers and proliferative diseases (Parsons et al., Nature 436:792 (2005); Hennessey at el., Nature Rev. Drug Disc. 4:988-1004 (2005)).

Further, over-activation of mitogen-activated protein (MAP) kinase cascade is known to play an important role in cell proliferation and differentiation. This pathway can be activated when a growth factor binds to its receptor tyrosine kinase. This interaction promotes RAS association with RAF and initiates a phosphorylation cascade through mitogen activated protein kinase (MEK) to ERK. Phosphorylation of MEK appears to increase its affinity and its catalytic activity toward ERK as well as is affinity for ATP.

The MAP kinase pathway is deregulated, often through mutations that result in ectopic protein activation, in roughly ⅓ of human cancers. This deregulation in turn results in a wide array of cellular changes that are integral to the etiology and maintenance of a cancerous phenotype including, but not limited to, the promotion of proliferation and evasion of apoptosis (Dhillon et al., Oncogene, 2007, 26: 3279-3290). Inhibition of this pathway is known to be beneficial in proliferative diseases. MEK is an attractive therapeutic target because the only known substrates for MEK phosphorylation are the MAP kinases, ERK1 and ERK2. MEK is frequently activated in tumors that have mutations in the RAS or RAF oncogenes. Constitutive activation of MEK/ERK has been found in pancreatic, colon, lung, kidney and ovarian primary tumor samples.

Inhibition of MEK has been shown to have potential therapeutic benefit in various diseases in several studies such as: (a) Tumor and Leukemia: Evidence of Efficacy in Tumor Models (Nature-Medicine 5(7): 810-816, 1999; Tracet et al, AACR Apr. 6-10, 2002, Poster #5426; Tecle, H. IBC 2$^{nd}$ International Conference of Protein Kinases, Sep. 9-10, 2002, J. Clin. Invest. 108(6), 851-859, 2001), (b) Pain: Evidence of Efficacy in Pain Models (J. Neurosci. 22:478, 2002; Acta Pharmacol Sin. 26:789 2005; Expert Opin Ther Targets. 9:699, 2005; Mol. Pain. 2:2, 2006), (c) Stroke: Evidence of Efficacy in Stroke Models Significant Neuroprotection against Ischemic Brain Injury by Inhibition of the MEK (J. Pharmacol. Exp. Ther. 304:172, 2003; Brain Res. 996:55, 2004), (d) Diabetes: Evidence In Diabetic Complications. (Am. J. Physiol. Renal. 286, F120 2004), (e) Inflammation: Evidence of Efficacy in Inflammation Models. (Biochem Biophy. Res. Com. 268:647, 2000), and (f) Arthritis: Evidence of efficacy in experimental osteoarthritis. (Arthritis & (J. Clin. Invest. 116:163. 2006).

The PI3K pathway interacts extensively with the MAPK pathway. These pathways share common upstream activators, and they are both activated by oncogenic RAS and appear to provide some compensatory signaling when one or the other is inhibited.

In spite of numerous treatment options for patients with cancer, there remains a need for effective and safe therapeutic agents and a need for new combination therapies that can be administered for the effective long-term treatment of cancer. It has been surprisingly discovered that the combination of an effective amount of the p110α-specific phosphatidylinositol 3-kinase (PI3K) inhibitor compound (S)-pyrrolidine-1,2-dicarboxylic acid 2-amide 1-(4-methyl-5-[2-(2,2,2-trifluoro-1,1-dimethyl-ethyl)-pyridin-4-yl]-thiazol-2-yl)-amide with an effective amount of at least one MEK inhibitor compound of the present invention, in particular 6-(4-bromo-2-fluorophenylamino)-7-fluoro-3-methyl-3H-benzoimidazole-5-carboxylic acid (2-hydroxyethoxy)-amide or (S)-5-fluoro-2-(2-fluoro-4-(methylthio)phenylamino)-N-(2-hydroxypropoxy)-1-methyl-6-oxo-1,6-dihydropyridine-3-carboxamide, results in unexpected improvement in the treatment of proliferative diseases, particularly cancer. When administered simultaneously, sequentially or separately, this specific phosphatidylinositol 3-kinase (PI3K) inhibitor compound and the MEK inhibitor compound of the present invention interact in a synergistic manner to strongly inhibit cell proliferation. This unexpected synergistic reaction allows reduction in the dose required for each compound, leading to a reduction in the side effects and enhancement of the long-term clinical effectively of the compounds in treatment.

SUMMARY OF THE INVENTION

The present invention relates to a pharmaceutical combination comprising: (a) a phosphatidylinositol 3-kinase (PI3K) inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one mitogen activated protein kinase (MEK) inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier for simultaneous, separate or sequential administration, in particular for treating or preventing a proliferative disease.

In a preferred embodiment of the present invention, the combination partners are (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound selected from the group consisting of 6-(4-bromo-2-fluorophenylamino)-7-fluoro-3-methyl-3H-benzoimidazole-5-carboxylic acid (2-hydroxyethoxy)-amide (COMPOUND B) or (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) or a pharmaceutically acceptable salt thereof.

In another preferred embodiment of the present invention, the combination partners are (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) or a pharmaceutically acceptable salt thereof.

The present invention further relates to a combined preparation or a pharmaceutical composition comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier. In one embodiment, the present invention relates to a combined preparation which comprises: (a) one or more unit dosage forms of combination partner (a), and (b) one or more unit dosage forms of combination partner (b).

The present invention particularly pertains to a pharmaceutical combination comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier useful for treating or preventing a proliferative disease in a subject in need thereof.

The present invention also pertains to a pharmaceutical combination comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier for use in the preparation of a pharmaceutical composition or medicament for the treatment or prevention of a proliferative disease in a subject in need thereof.

The present invention further pertains to the use of a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, in combination with at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof for the preparation of a pharmaceutical composition or medicament for the treatment or prevention of a proliferative disease.

The present invention relates to a method of treating a subject having a proliferative disease comprising administered to said subject a combination comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier in a quantity, which is jointly therapeutically effective against a proliferative disease.

The present invention further provides a commercial package comprising as therapeutic agents a combination comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, together with instructions for simultaneous, separate or sequential administration thereof for use in the delay of progression or treatment of a proliferative disease.

DETAILED DESCRIPTION OF THE INVENTION

Figure 1:
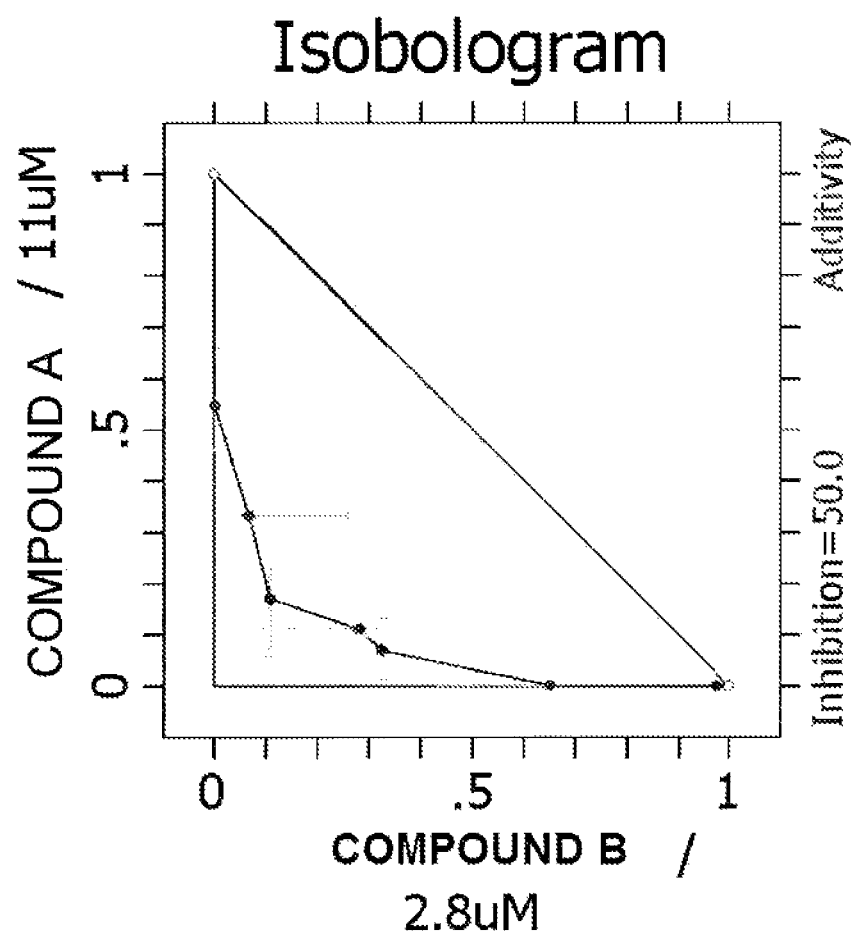
FIG. 1 shows the isobologram contour at 50% inhibition for the combination with (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) and 6-(4-bromo-2-fluorophenylamino)-7-fluoro-3-methyl-3H-benzoimidazole-5-carboxylic acid (2-hydroxyethoxy)-amide (COMPOUND B) in NCI—H2122 non-small cell lung cancer cell lines.

The present invention relates to a pharmaceutical combination comprising: (a) a phosphatidylinositol 3-kinase (PI3K) inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (hereinafter, referred to as "COMPOUND A"), or a pharmaceutically acceptable salt thereof, and (b) at least one mitogen activated protein kinase (MEK) inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier, for simultaneous, separate or sequential administration, in particular for use in the treatment or prevention of a proliferative disease.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover bot the singular and the plural, unless otherwise indicated herein or clearly contradicted by context. Where the plural form is used for compounds, salts, and the like, this is taken to mean also a single compound, salt, or the like.

The term "combination" or "pharmaceutical combination" is defined herein to refer to either a fixed combination in one dosage unit form, a non-fixed combination or a kit of parts for the combined administration where COMPOUND A or a pharmaceutically acceptable salt thereof, and at least one MEK inhibitor compound or a pharmaceutically acceptable salt thereof may be administered simultaneously, independently at the same time or separately within time intervals that allow that the combination partners show a cooperative, e.g., synergistic, effect. The term "fixed combination" means that the active ingredients, e.g. a COMPOUND A and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The term "a phosphatidylinositol 3-kinase inhibitor" is defined herein to refer to a compound which targets, decreases or inhibits PI 3-kinase. PI 3-kinase activity has been shown to increase in response to a number of hormonal and growth factor stimuli, including insulin, platelet-derived growth factor, insulin-like growth factor, epidermal growth factor, colony-stimulating factor, and hepatocyte growth factor, and has been implicated in processes related to cellular growth and transformation.

The term "a MEK inhibitor" is defined herein to refer to a compound which targets, decreases or inhibits the kinase activity of MAP kinase, MEK. A target of a MEK inhibitor includes, but is not limited to, ERK. An indirect target of a MEK inhibitor includes, but is not limited to, cyclin D1.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "co-administration" or "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject.

The term "prevent", "preventing" or "prevention" as used herein comprises the prevention of at least one symptom associated with or caused by the state, disease or disorder being prevented.

The term "jointly therapeutically active" or "joint therapeutic effect" as used herein means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both compounds are present in the blood of the human to be treated at least during certain time intervals.

The term "pharmaceutically effective amount" or "clinically effective amount" of a combination of therapeutic agents is an amount sufficient to provide an observable improvement over the baseline clinically observable signs and symptoms of the disorder treated with the combination.

The term "synergistic effect" as used herein refers to action of two therapeutic agents such as, for example, a compound of formula (I), e.g., Compound A, and at least one MEK inhibitor compound of the present invention, producing an effect, for example, slowing the symptomatic progression of a proliferative disease, particularly cancer, or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from cancers.

The term about" or "approximately" shall have the meaning of within 10%, more preferably within 5%, of a given value or range.

Pharmaceutical combinations of the present invention include a phosphatidylinositol 3-kinase inhibitor (PI3K) compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (hereafter, referred to as ("COMPOUND A"). COMPOUND A is a p110α-selective phosphatidylinositol 3-kinase (PI3K) inhibitor compound of Formula I

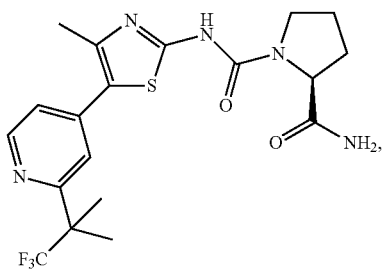

(I)

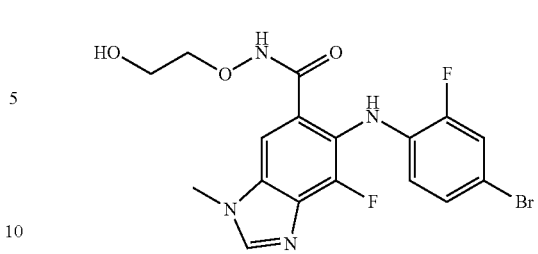

(II)

COMPOUND A was originally described in WO 2010/029082, wherein the synthesis of its free base form was described. The synthesis of COMPOUND A is for instance described in WO 2010/029082, which is hereby incorporated by reference in its entirety, as Example 15.

When referring to COMPOUND A, the term "salt" or "salts" is understood to be a salt of COMPOUND A that can be present alone or in mixture with free compound of Formula (I) and are preferably pharmaceutically acceptable salts. Such salts are formed, for example, as acid addition salts, preferably with organic or inorganic acids, from the compound of Formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient. The salts of COMPOUND A are preferably pharmaceutically acceptable salts; suitable counter-ions forming pharmaceutically acceptable salts are known in the field.

Pharmaceutical combinations of the present invention include at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof.

The MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) is a compound of formula (II)

The MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) is described in PCT Application No. WO 03/077914, and methods for its preparation have been described, for example, in Example 18 therein.

Except as herein disclosed, the compounds used in the present invention may possess one or more asymmetric centers and can be produced as individual (R)- or (S)-stereoisomers or as mixtures thereof as described in PCT Application No. WO03/077914. Except as otherwise indicated, the description or naming of a particular compound in the specification and claims is intended to include both individual enantiomers, diastereomeric mixtures, racemic or otherwise, thereof. Accordingly, this invention also includes all such isomers, including diasteroemeric mixtures ad resolved enantiomers of the compounds of this invention. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced organic Chemistry", 4$^{th}$ edition, J. March. John Wiley and Sons, New York, 1992).

The MEK inhibitor compound (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) is a compound of formula (III)

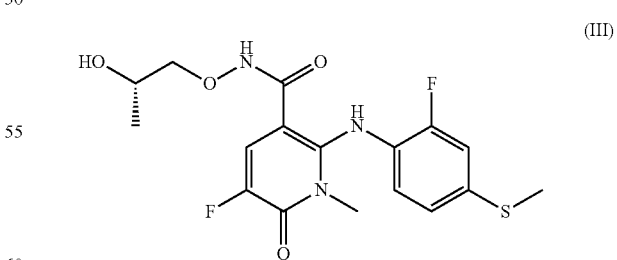

(III)

The MEK inhibitor compound (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) is described in Example 25-BB of PCT Application No. WO2007/044084, and methods for its preparation have been described therein.

Additional MEK inhibitors that may be used in the combination of the present invention include, but are not limited to, PD0325901 (Pfizer)(See PCT Publication No. WO02/06213), PD-184352 (Pfizer), RDEA119 (Ardea Biosciences), GSK1120212 (GlaxoSmithKline)(See PCT Publication No. WO05/121142), XL518 (Exelexis), AS-701255 (Merck Serono), AS-701173 (Merck Serono), AS703026 (Merck Serono), RDEA436 (Ardea Biosciences, E6201 (Eisai)(See Goto et al, Journal of Pharmacology and Experimental Therapeutics, 3331(2): 485-495 (2009)), RO4987655 (Hoffmann-La Roche), JTP-74057, RG7167, and/or RG7420

Preferably, the MEK inhibitor compound used in the combination of the present invention is selected from the group consisting of 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), or a pharmaceutically acceptable salt thereof.

As related to the MEK inhibitors, the term "salt" or "salts", unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. Since a single compound of the present invention may include more than one acidic or basic moieties, the compounds of the present invention may include mono, di or tri-salts in a single compound.

In the case of an acidic moiety in a compound of the present invention, a salt may be formed by treatment of a compound of the present invention with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of the present invention.

With respect to basic moieties, a salt is formed by the treatment of a compound of the present invention with an acidic compound, particularly an inorganic acid. Preferred inorganic salts of this type may include, for example, the hydrochloric, hydrobromic, sulfuric, phosphoric or the like salts. Preferred organic salts of this type, may include, for example, salts formed with acetic, succinic, citric, maleic, fumaric, D-glutamic, glycolic, benzoic, cinnamic and the like organic acids. An especially preferred salt of this type is a hydrochloride or sulfate salt of COMPOUND B of the present invention.

Additional pharmaceutically acceptable salts of COMPOUND B and COMPOUND C suitable for the present invention include the salts disclosed in PCT Application No. WO 03/077914 and PCT Application No. WO2007/044084, which are both hereby incorporated into the present application by reference.

Unless otherwise specified, or clearly indicated by the text, reference to therapeutic agents useful in the pharmaceutical combination of the present invention includes both the free base of the compounds, and all pharmaceutically acceptable salts of the compounds.

The structure of the compounds identified by code nos., generic or trade names may be taken from the actual edition of the standard compendium "The Merck Index" or from databases, e.g., Patents International (IMS World Publications). The corresponding content thereof is hereby incorporated by reference.

In each case where citations of patent applications are given above, the subject matter relating to the compounds is hereby incorporated into the present application by reference. The compounds used as therapeutic agents in the pharmaceutical combinations of the present invention can be prepared and administered as described in the cited documents, respectively. Also within the scope of this invention is the combination of two separate therapeutic agents as set forth above, i.e., a pharmaceutical combination within the scope of this invention could include three therapeutic agents or more.

A pharmaceutical combination which comprises (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A), or a pharmaceutically acceptable salt thereof, and (b) at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier, will be referred to hereinafter as a COMBINATION OF THE INVENTION.

In a preferred embodiment of the present invention, the combination partners are (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound selected from the group consisting of 6-(4-bromo-2-fluorophenylamino)-7-fluoro-3-methyl-3H-benzoimidazole-5-carboxylic acid (2-hydroxyethoxy)-amide (COMPOUND B) or (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) or a pharmaceutically acceptable salt thereof.

In another preferred embodiment of the present invention, the combination partners are (a) a PI3K inhibitor compound ((S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) or a pharmaceutically acceptable salt thereof.

The present invention also pertains to a combined preparation or a pharmaceutical composition comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier.

In one embodiment, the present invention relates to a combined preparation which comprises: (a) one or more unit dosage forms of combination partner (a), and (b) one or more unit dosage forms of combination partner (b).

The present invention particularly pertains to a COMBINATION OF THE INVENTION useful for treating or preventing a proliferative disease in a subject in need thereof. In this embodiment of the present invention, the COMBINATION OF THE INVENTION is used for the treatment or prevention of a proliferative disease comprising administering to the subject a combination therapy, comprising an effective amount of a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof. Preferably, the MEK inhibitor compound is administered at therapeutically effective dosages which, when combined, provide a beneficial effect. The administration may be simultaneous or sequential.

The proliferative disease treated or prevented by the COMBINATION OF THE INVENTION is mainly tumor and/or cancer. Examples of proliferative diseases include melanoma, lung cancer, colorectal cancer (CRC), breast cancer, kidney cancer such as e.g. renal cell carcinoma (RCC), liver cancer or hepatocellular carcinoma, acute myelogenous leukemia (AML), myelodysplastic Syndromes (MDS), non-small-cell lung cancer (NSCLC), thyroid cancer, pancreatic cancer, esophageal, and neurofibromatosis.

In a one embodiment of the present invention, the proliferative disease is a solid tumor. The term "solid tumor" especially means melanoma, thyroid cancer, breast cancer, pancreatic cancer, ovarian cancer, cancer of the colon and generally the GI (gastro-intestinal) tract, cervix cancer, kidney cancer such as e.g., renal cell carcinoma (RCC), liver cancer or hepatocellular carcinoma, lung cancer, in particular small-cell lung cancer and non-small-cell lung cancer, head and neck cancer, bladder cancer, cancer of the prostate, esophageal, or Kaposi's sarcoma. The present combination inhibits the growth of solid tumors, but also liquid tumors. Furthermore, depending on the tumor type and the particular combination used a decrease of the tumor volume can be obtained. The combinations disclosed herein are also suited to prevent the metastatic spread of tumors and the growth or development of micrometastases. The combinations disclosed herein are in particular suitable for the treatment of poor prognosis patients, especially such poor prognosis patients having metastatic melanome or pancreatic cancer.

The cancer to be treated can have a overexpression or amplification of PI3K alpha, mutations of PIK3CA, and/or genetic alteration in the MAP signal transduction pathway such as e.g. a HRAS, KRAS, NRAS or BRAF mutation or gene amplification. In one embodiment the cancer to be treated has a KRAS mutation, e.g. KRAS mutated pancreas cancer, colon cancer, lung cancer (e.g. NSCLC) or leukemias.

In a further embodiment, the proliferative disease is pancreatic cancer, colorectal cancer, melanoma, esophageal, or lung cancer, particularly non-small cell lung cancer.

It will be understood that the COMBINATION OF THE INVENTION may be used solely for the treatment of a proliferative disease in accordance with the present invention.

It has been found that the combination therapy comprising a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, particularly 6-(4-bromo-2-fluorophenylamino)-7-fluoro-3-methyl-3H-benzoimidazole-5-carboxylic acid (2-hydroxyethoxy)-amide (COMPOUND B) or (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), or a pharmaceutically acceptable salt thereof, results in unexpected improvement in the treatment or prevention of proliferative diseases as compared to the monotherapy. When administered simultaneously, sequentially or separately, the PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) and the MEK inhibitor interact synergistically to inhibit cell proliferation. The COMBINATION OF THE INVENTION is in particular suitable for the treatment of patients with advanced cancer who have failed standard systemic therapy. This includes patients having tumor types showing resistance to monotherapy or showing resistance to combinations different from those disclosed herein.

The nature of proliferative diseases is multifactorial. Under certain circumstances, drugs with different mechanisms of action may be combined. However, just considering any combination of therapeutic agents having different mode of action does not necessarily lead to combinations with advantageous effects.

The administration of a pharmaceutical combination of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically therapeutic agents used in the combination of the invention.

A further benefit is that lower doses of the therapeutic agents of the COMBINATION OF THE INVENTION can be used, for example, that the dosages need not only often be smaller, but are also applied less frequently, or can be used in order to diminish the incidence of side-effects observed with one of the combination partners alone. This is in accordance with the desires and requirements of the patients to be treated.

It can be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in a test procedure as essentially described hereinafter.

Suitable clinical studies are in particular, for example, open label, dose escalation studies in patients with a proliferative diseases. Such studies prove in particular the synergism of the therapeutic agents of the COMBINATION OF THE INVENTION. The beneficial effects on proliferative diseases may be determined directly through the results of these studies which are known as such to a person skilled in the art. Such studies may be, in particular, be suitable to compare the effects of a monotherapy using either therapeutic agent and a COMBINATION OF THE INVENTION.

In one embodiment, the dose of the PI3K inhibitor COMPOUND A is escalated until the Maximum Tolerated Dosage is reached, and at least one MEK inhibitor compound of the present invention is administered with a fixed dose. Alternatively, the PI3K inhibitor COMPOUND A may be administered in a fixed dose and the dose of at least MEK inhibitor of the present invention may be escalated. Each patient may receive doses of the PI3K inhibitor COMPOUND A and/or at least one MEK inhibitor of the present invention either daily or intermittently. The efficacy of the treatment may be determined in such studies, e.g., after 12, 18 or 24 weeks by evaluation of symptom scores every 6 weeks.

In a preferred embodiment, the MEK inhibitor is COMPOUND B or COMPOUND C or a pharmaceutically acceptable salt thereof.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in one species can be predictive of the effect in other species and animal models exist, as described herein, to measure a synergistic effect and the results of such studies can also be used to predict effective dose and plasma concentration ratio ranges and the absolute doses and plasma concentrations required in other species by the application of pharmacokinetic/pharmacodynamic methods. Established correlations between tumor models and effects seen in man suggest that synergy in animals may, e.g., be demonstrated in the BRAF mutant: SW1417, COLO205, LS411N, HCT-29, and RKO; KRAS mutant: NCI—H23, NCI—H2122, NCI—H358, NCI—H460, HCT-15, SW480, SW620, SW837, COLO-678, LS123, NCI—H747, HCT-116, T84, LS180, SW948, and GP2d; PIK3CA mutant: NCI—H460, HCT-15, HCT-116, HCT-29, RKO, T84, SW48; and TP53 mutant: C2BBe1 cancer tumor models as described in the Examples below.

In a preferred embodiment of the present invention, the COMBINATION OF THE INVENTION comprises a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and at least one MEK inhibitor compound selected from the group comprising 6-(4-bromo-2-fluorophenylamino)-7-fluoro-3-methyl-3H-benzoimidazole-5-carboxylic acid (2-hydroxy-ethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, and/or RG7420 or a pharmaceutically acceptable salt thereof, for use in the treatment or prevention of a proliferative disease, preferably a cancer, comprising an overexpression or amplification of PI3K alpha, PIK3CA mutations, and/or HRAS, KRAS, NRAS or BRAF mutation. Preferably, the cancer comprising an overexpression or amplification of PI3K alpha, PIK3CA mutations, and/or HRAS, KRAS, NRAS or BRAF mutation is melanoma, pancreatic, colorectal, esophageal, or lung.

In one aspect, the present invention provides a synergistic combination for human administration comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound of the present invention, preferably COMPOUND B, or a pharmaceutically acceptable salt thereof, in a combination range (w/w) which corresponds to the ranges observed in a tumor model, e.g., as described in the Examples below, used to identify a synergistic interaction. Suitably, the ratio range in humans corresponds to a non-human range selected from between 50:1 to 1:50 parts by weight, 50:1 to 1:20, 50:1 to 1:10, 50:1 to 1:1, 20:1 to 1:50, 20:1 to 1:20, 20:1 to 1:10, 20:1 to 1:1, 10:1 to 1:50, 10:1 to 1:20, 10:1 to 1:10, 10:1 to 1:1, 1:1 to 1:50, 1:1 to 1:20 and 1:1 to 1:10. More suitably, the human range corresponds to a non-human range of the order of 10:1 to 1:1, 5:1 to 1:1 or 2:1 to 1:1 parts by weight.

In another aspect, the present invention provides a synergistic combination for human administration comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound of the present invention, preferably COMPOUND B, or a pharmaceutically acceptable salt thereof, in a combination range (w/w) which corresponds to the ranges observed in a tumor model, e.g., as described in the Examples below, used to identify a synergistic interaction.

According to a further aspect, the present invention provides a synergistic combination for administration to humans comprising (a) a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound of the present invention, preferably COMPOUND B, or a pharmaceutically acceptable salt thereof, where the dose range of each component corresponds to the synergistic ranges observed in a suitable tumor model, e.g., the tumor models described in the Examples below, primarily used to identify a synergistic interaction.

It is one objective of this invention to provide a pharmaceutical composition comprising a quantity, which is jointly therapeutically effective against a proliferative disease comprising the COMBINATION OF THE INVENTION. In this composition, the combination partners (a) and (b) can be either administered in a single formulation or unit dosage form, administered concurrently but separately, or administered sequentially by any suitable route. The unit dosage form may also be a fixed combination.

The pharmaceutical compositions for separate administration of both combination partners, or for the administration in a fixed combination, i.e. a single galenical composition comprising the COMBINATION OF THE INVENTION, may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers, especially suitable for enteral or parenteral application.

The novel pharmaceutical composition contains may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

A unit dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

The unit dosage forms of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients*, 4$^{th}$ edition, Rowe et al., Eds., American Pharmaceuticals Association (2003); and *Remington: the Science and Practice of Pharmacy*, 20$^{th}$ edition, Gennaro, Ed., Lippincott Williams & Wilkins (2003).

These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

In one embodiment, the present invention also pertains to a COMBINATION OF THE INVENTION for use in the preparation of a pharmaceutical composition or medicament for the treatment or prevention of a proliferative disease in a subject in need thereof.

In a further embodiment, the present invention pertains to the use of a PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, for the preparation of a pharmaceutical composition or medicament for the treatment or prevention of a proliferative disease in a subject in need thereof. Preferred is a MEK inhibitor selected from 6-(4-bromo-2-fluorophenylamino)-7-fluoro-3-methyl-3H-benzoimidazole-5-carboxylic acid (2-hydroxyethoxy)-amide (COMPOUND B) or (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C).

In accordance with the present invention, a therapeutically effective amount of each of the combination partner of the COMBINATION OF THE INVENTION may be administered simultaneously or sequentially and in any order, and the components may be administered separately or as a fixed combination. For example, the method of treating a proliferative disease according to the invention may comprise (i) administration of the first agent (a) in free or pharmaceutically acceptable salt form and (ii) administration of an agent (b) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the COMBINATION OF THE INVENTION may be administered separately at different times during the course of therapy or concurrently in divided or single combination forms. Furthermore, the term "administering" also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single therapeutic agents required to alleviate, counter or arrest the progress of the condition.

The optimum ratios, individual and combined dosages, and concentrations of the combination partners (a) and (b) of the COMBINATION OF THE INVENTION that yield efficacy without toxicity are based on the kinetics of the therapeutic agents' availability to target sites, and are determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the combination partners, which are employed in the COMBINATION OF THE INVENTION, are applied in the form as marketed as single drugs, their dosage and mode of administration can be in accordance with the information provided on the package insert of the respective marketed drug, if not mentioned herein otherwise.

The PI3K inhibitor compound COMPOUND A may administered to a suitable subject daily in single or divided doses at an effective dosage in the range of about 0.05 to about 50 mg per kg body weight per day, preferably about 0.1-25 mg/kg/day, more preferably from about 0.5-10 mg/kg/day, in single or divided doses. For a 70 kg human, this would amount to a preferable dosage range of about 35-700 mg per day The MEK inhibitor compound COMPOUND B may be administered to a suitable subject daily in single or divided doses at an effective dosage in the range of about 0.001 to about 100 mg per kg body weight per day, preferably about 1 to about 35 mg/kg/day, in single or divided doses. For a 70 kg human, this would amount to a preferable dosage range of about 0.05 to 7 g/day, preferably about 0.05 to about 2.5 g/day.

The MEK inhibitor compound COMPOUND C may be administered daily to a suitable subject in single or divided doses at an effective dosage in the range of about 0.001 to about 100 mg per kg body weight per day, preferably about 1 mg/kg/day to about 35 mg/kg/day, in single or divided doses. For a 70 kg human, this would amount to a preferable dosage range of about 0.07 to 2.45 g/day, preferably about 0.05 to about 1.0 g/day.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The present invention relates to a method of treating a subject having a proliferative disease comprising administered to said subject a COMBINATION OF THE INVENTION in a quantity, which is jointly therapeutically effective against a proliferative disease. In particular, the proliferative disease to be treated with a COMBINATION OF THE INVENTION is a melanoma, colorectal cancer or lung cancer, particularly non-small cell lung cancer. Furthermore, the treatment can comprise surgery or radiotherapy.

The present invention further relates to the COMBINATION OF THE INVENTION for use in the treatment of a proliferative disease, particularly cancer.

The present invention further provides a commercial package comprising as therapeutic agents COMBINATION OF THE INVENTION, together with instructions for simultaneous, separate or sequential administration thereof for use in the delay of progression or treatment of a proliferative disease in a subject in need thereof.

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1

Materials and Methods

The colorectal cancer cell lines SW1417, COLO 205, LS411N, HT-29, RKO, OUMS-23, SW620, LoVo, SW480, SW837, COLO-678, LS123-NCI—H747, HCT-15, HCT116, DLD-1, T84, SW948, LS180, GP2d, HuTu 80, CW-2, SW48, NCI—H716, C2Bbe1, SNU—C1 and KM12 are obtained from the American Type Culture Collection (ATCC) and maintained in their respective culture medium as specified by the provider. These colorectal cancer cell lines have the following mutation status:

For assessment of combination effects, cells are seeded into 384-well plates at 500 cells/well and incubated overnight. The contents of the compound master plates are pre-diluted with 1:200 (1 μL compound solution to 200 μL cell RPMI-160 culture medium containing 10% fetal clf serum) before transferring 5 μL of this pre-dilution to the cell plates containing 20 μL cell culture medium, to achieve the targeted final compound concentrations as well as a vehicle (DMSO) concentration of 0.09%.

Effects of single agents as well as their checkerboard combinations on cell viability are assessed after 72 hours of incubation at 37° C./5% $CO_2$ by quantification of cellular ATP levels (CellTiterGlo, Promega) using 25 μL reagent/well and n=2 repliate plates per condition. The number/viability of cells at the time of compound addition was likewise assessed and used to estimate the population doubling time of the particular cell line. Single agent IC50s are calculated using standard four-parametric curve fitting (SLFit, model 205). Potential synergistic interactions between compound combinations are assessed using the Excess Inhibition 2D matrix according to the Loewe additivity model and are reported as Synergy Score. In addition, compound combinations are assessed by combination index analysis derived from isobologram graphs at 50% inhibition, and are reported as best combination index (CI), which corresponds to the lowest value on the isobologram. All synergy calculations are performed using CHALICE software (Lehár et al, Nat Biotechnol. (July 2009), 27(4): 69:66). Interpretation of values for combination index and synergy score are provided below:

| Cell-line Name | BRAF | KRAS | NRAS | PIK3CA | PTEN | TP53 | CDKN2A |
|---|---|---|---|---|---|---|---|
| SW1417 | mut | wt | wt | wt | wt | mut | wt |
| COLO 205 | mut | wt | wt | wt | wt | mut | wt |
| LS411N | mut | wt | wt | wt | wt | mut[#] | wt |
| HT-29 | mut | wt | wt | mut[#] | wt | mut | wt |
| HT-29* | mut | wt | wt | mut[#] | wt | mut | wt |
| RKO | mut | wt | wt | mut | wt | wt | wt |
| OUMS-23 | mut | wt | wt | wt | mut[§] | wt | nd |
| SW620 | wt | mut | wt | wt | wt | mut | wt |
| LoVo | wt | mut | wt | wt | wt | wt | mut[§] |
| SW480 | wt | mut | wt | wt | wt | mut | wt |
| SW837 | wt | mut | wt | wt | wt | mut | wt |
| COLO-678 | wt | mut | wt | wt | wt | wt | mut |
| LS123 | wt | mut | wt | wt | wt | mut[#] | mut |
| NCI-H747 | wt | mut | wt | wt | wt | mut[#] | wt |
| HCT-15 | wt | mut | wt | mut | wt | mut | wt |
| HCT 116 | wt | mut | wt | mut | wt | wt | mut |
| HCT 116* | wt | mut | wt | mut | wt | wt | mut |
| DLD-1 | wt | mut | wt | mut | wt | mut | wt |
| T84** | wt | mut | wt | mut | wt | mut | wt |
| SW948** | wt | mut | wt | mut | wt | wt | wt |
| LS 180 | wt | mut | wt | mut | wt | wt | nd |
| GP2d | wt | mut | wt | mut | wt | wt | wt |
| HuTu 80 | wt | wt | wt | wt | wt | wt | wt |
| CW-2 | wt | wt | wt | wt | wt | wt | wt |
| SW48 | wt | wt | wt | mut[#] | wt | wt | wt |
| NCI-H716 | wt | wt | wt | wt | wt | mut | wt |
| C2BBe1 | wt | wt | wt | wt | wt | mut | wt |
| SNU-C1 | wt | wt | wt | wt | wt | mut | wt |
| KM12 | wt | wt | wt | wt | mut | mut | wt |

Mutation (mut) and wildtype (wt) represent known functionally relevant mutations.
mut[§] is based upon lack of expression from analysis.
mut[#] designates a mutation with unknown functional significance.
Nd designates no data.
*designates a repeat experiment performed at end of study, wherein the data was excluded from calculation of median and mean.
**designates duplicate data points and dose response that display some scatter.

| Combination Index (CI) | Synergy Score |
| --- | --- |
| CI = 1 → Dose additive | S~0 → Dose additive |
| CI < 0.5 → "real" synergy (2x dose shift) | S > 2 $\sigma_S$ → Real synergy detected |
| CI < 0.3 → "useful" synergy (3x shift) | S > 1 → Usually indicating Synergy |
| CI < 0.1 → "strong" synergy (10x shift) | |

Pairwise multiple comparisons of the result groups are performed by one-way ANOVA (Neuman-Keuls method) using GraphPad Prism 5 (GraphPad Software Inc.).

Results

For this study, a summary of the main results in all of the colorectal cell lines are shown as follows:

| Cell line name | Cmpd. B IC50 [nM] | Cmpd. A IC50 [nM] | Synergy Score | Best C.I. (at 50% inhibition) | Effect Description |
| --- | --- | --- | --- | --- | --- |
| SW1417 | 53.9 | 7850 | 3.15 | 0.25 | Synergy |
| COLO205 | 34.4 | >10800 | 2.68 | 0.62 | Additive/Synergy |
| LS411N | 54.7 | 8670 | 2.89 | 0.52 | Additive/Synergy |
| HT-29 | 84.0 | 5200 | 4.57 | 0.35 | Synergy |
| HT-29* | 66.5 | 4280 | 4.68 | 0.39 | Synergy |
| RKO | >2700 | 6730 | 4.08 | 0.25 | Synergy |
| OUMS-23 | >2700 | >10800 | 0.20 | Nc | Na |
| SW620 | 26.9 | >10800 | 2.93 | 0.36 | Synergy |
| LoVo | 148 | 8660 | 1.61 | 1.15 | Additive |
| SW480 | 2030 | 9350 | 1.95 | 0.37 | Additive/Synergy |
| SW837 | 557 | 7280 | 2.39 | 0.54 | Additive/Synergy |
| COLO-678 | 1710 | >10800 | 2.06 | 0.31 | Synergy |
| LS123 | 2280 | 7250 | 3.02 | 0.36 | Synergy |
| NCI-H747 | 153 | 6210 | 4.07 | 0.30 | Synergy |
| HCT-15 | >2700 | 6720 | 2.04 | 0.56 | Additive/Synergy |
| HCT 116 | 881 | 9420 | 6.53 | 0.13 | Synergy |
| HCT 116* | 735 | 8320 | 7.67 | 0.13 | Synergy |
| DLD-1 | >2700 | >10800 | 1.99 | Nc | Na |
| T84** | 12800 | 4160 | 5.39 | 0.40 | Synergy |
| SW948** | 89.8 | 1190 | 4.36 | 0.60 | Additive/Synergy |
| LS 180 | 143 | 5080 | 3.89 | 0.40 | Synergy |
| GP2d | 756 | 698 | 4.79 | 0.11 | Synergy |
| HuTu 80 | >2700 | 8840 | 1.68 | 0.96 | Additive |
| CW-2 | >2700 | >10800 | 1.19 | Nc | Na |
| SW48 | 78.4 | 1410 | 7.89 | 0.24 | Synergy |
| NCI-H716 | >2700 | >10800 | 3.91 | 0.22 | Synergy |
| C2BBe1 | 1580 | 9200 | 2.17 | 0.42 | Synergy |
| SNU-C1 | 15.1 | 2430 | 3.66 | 0.39 | Synergy |
| KM12 | 339 | >10800 | 049 | 0.99 | Additive |
| Median | 76 | 8660 | 2.93 | 0.38 | |
| Mean | 1160 | 7510 | 3.17 | 0.45 | |

The PI3K inhibitor COMPOUND A and MEK inhibitor COMPOUND B shows synergistic interactions in 17 out of the 27 tested colorectal cancer cell lines. On average, the highest degree of synergy in cell lines with PIK3CA mutations. Except for cell lines null for PTEN, the mutation status of the key MAP kinase (BRAF/KRAS) or PI3K (PIK3CA/PTEN) pathway notes had no statistically significant influence on the observed synergy score. In summary, these results suggest synergistic interaction for COMPOUND A and COMPOUND B in colorectal cell lines wild-type or mutated for BRAF, KRAS and PIK3CA, but not those null for PTEN.

Example 2

Material and Methods

The cell lines used in this study were purchased from American Type Cell Collection, including non-small cell lung cancer cell lines NCI—H23 & NCI—H2122 (which carry both KRAS and LKB1 mutations), NCI—H358 (which carries KRAS mutation), NCI—H460 (which carries KRAS, LKB1 and PIK3CA mutations), and Colorectal Cancer cell line SW480 (which carries KRAS mutation), HCT-15 (which carries KRAS PIK3CA mutations). All the cell lines were cultured at 37° C. in a 5% $CO_2$ incubator in RPMI 1640 (ATCC #30-2001) media complemented with 10% fetal bovine serum, 2 mmol/L glutamine and 1% sodium pyruvate.

Cell Proliferation Assay:

Cell viability was determined by measuring cellular ATP content using the CellTiter-Glo® Luminescent Cell Viability Assay (Promega #G7573) according to manufacturer's protocol. Briefly, 500-900 cells/well were plated on clear-bottom 384-well black plates (Greiner#781091) in quadruplicates or duplicates with 30 ul/well growth media, cells were allowed to attach overnight and followed by 72 hrs of incubation with various concentration of drugs or drug combinations (10 ul/well), at the end of the drug treatment, 30 ul/well of the CellTiter-Glo regent were added to each well to lyse the cells, and luminescence signals were recorded on a Envision plate reader.

Method for Calculating the Effect of the Combination:

To evaluate the COMPOUND B and COMPOUND A combination effect in a non-bias way and to identify synergistic effect at all possible concentrations, the combination studies were conducted with a "dose matrix", where a combination is tested in all possible permutations of serially-diluted COMPOUND B and COMPOUND A single agent doses, in all combination assays, compounds were applied simultaneously. This "dose matrix" is as following: COMPOUND B was subjected to an 11 dose 2× serial dilution with the highest dose at 5 µM and the low dose at about 5 nM, and COMPOUND A was subjected to a 9 dose 2× serial dilution with high dose at 5 µM and low dose at about 20 nM. Single agent dose responding curves, $IC_{50}$, $IC_{90}$, and the Synergy are all analyzed using Chalice software (CombinatoRx, Cambridge Mass.). Synergy was calculated by comparing a combination's response to those of its single agents, against the drug-with-itself dose-additive reference model. Deviations from dose additives can be assessed visually on an Isobologram or numerically with a Combination Index. Excess inhibition compare to additives can also be plotted as a full dose-matrix chart to capture where the synergies occur. To quantify the overall strength of combination effects, a volume score $V_{HSA} = \Sigma_{X,Y} \ln f_X \ln f_Y (I_{data} - I_{HSA})$ is also calculated between the data and the highest-single-agent surface, normalized for single agent dilution factors $f_X$, $f_Y$.

The Cell Proliferation Assay Results:

In summary, synergy was observed in all six cell lines examined, produced synergy scores ranging from 2.09 to 5.49, synergistic regions are broad and are typically observed for COMPOUND A at doses of above 150 nM and for COMPOUND B at doses of 80 nM and higher. These results suggest synergistic interaction potential for COMPOUND B and COMPOUND A in CRC and NSCLC cell lines that carry KRAS mutations.

| Cell Line | Synergy Score |
|---|---|
| HCT-15 | 3.05 |
| NCI-H358 | 4.26 |
| NCI-H23 | 3.50 |
| SW480 | 2.09 |
| NCI-H2122 | 5.49 |
| NCI-H460 | 3.11 |

Example 3

Material and Methods

Cell Line Testing:

The combination of PI3K inhibitor COMPOUND A and MEK inhibitor COMPOUND B, as defined above, was tested across 38 cell lines from three tissue types (7 pancreas, 10 lung, and 21 melanoma). Each combination was tested in a partially-filled "dose matrix" constructed as follows: Each single drug was dispensed into growth media at a top concentration (11 µM for COMPOUND A or 2.7 µM for COMPOUND B), and serially diluted by 3× to yield a 7 point series covering a factor of 729 in concentration. The compounds were then combined at all pairs of the $2^{nd}$ through the $6^{th}$ concentrations, and this dose matrix was extended by also combining the top and bottom concentrations with each other. Higher-resolution testing was also performed on some NSCLC cell lines, testing 9 doses of COMPOUND A and 11 doses of COMPOUND B, in each case using 2× dilutions starting at 5 µM. All the cell lines were cultured at 37° C. in a 5% $CO_2$ incubator in RPMI 1640 (American Type Cell Collection No. 30-2001) media complemented with 10% fetal bovine serum, 2 mmol/L glutamine and 1% sodium pyruvate. Each such dose matrix was tested in triplicate on separate assay plates. In order to identify cytotoxic treatments, we also determined "Day 0" cell populations at the start of drug treatment.

Measuring Combination Effects:

Cell responses at each treatment were measured using simple inhibitions I=1−T/V, where T is the treated well's raw response and V is the median untreated level between replicate wells on the plate. Cytotoxicity measurements were measured using a "Growth Inhibition" $GI=1-(T-V_0)/[T<V_0? V_0: (V-V_0)]$, where $V_0$ is the median Day 0 raw level, and the notation [C?A:B] yields A when condition C is true and B when it is false. GI=0, 1, and 2 correspond to ineffective, cytostatic, and completely cytotoxic treatments respectively. Using the Chalice analysis software (CombinatoRx, Cambridge Mass.), the agent responses were fitted to a sigmoidal function with dose, parameterized by the maximum effect $A_{max}$ at high doses, the transitional concentration $EC_{50}$, and Hill coefficient for the steepness of that transition, interpolated to a 50% inhibition crossing point $IC_{50}$. The combination effect was described using the maximum inhibition and GI value in the dose matrix, and by comparing a combination's responses to those of its single agents, via the dose-additive Loewe model. The "Synergy Score" $S_{Loewe}=\Sigma_{X,Y} \ln f_X \ln f_Y \max(0,I_{data}) \max(0,I_{data}-I_{Loewe})$ was calculated from the differences between the data $I_{data}$ and the dose-additive surface $I_{Loewe}$, across all combined concentrations X,Y, and weighted by the measured inhibition and the single agent dilution factors $f_X$, $f_Y$. In addition to synergy, the dose shifting at 50% inhibition was determined using a combination index $CI_{50}=C_X/IC_{50X}+C_Y/IC_{50Y}$, where $C_X$, $C_Y$ are the lowest concentrations of the single agents that yield 50% inhibition in combination, compared to the $Ic_{50}$ values of each compound.

The Cell Proliferation Assay Results

The resulting combination effects across the tested cell lines are shown in the table below, along with the lineage and mutation status for each cell line (mut=known driver lesion, mut?=unknown lesion, wt=wildtype).

| Cell Line | Lineage | PIK3CA | PTEN | KRAS | NRAS | BRAF | Synergy Score | Best CI (Inhib = 0.5) | Max. Inhib | Max. GI |
|---|---|---|---|---|---|---|---|---|---|---|
| AsPC-1 | Pancreas | wt | wt | mut | wt | wt | 3.45 | 0.18 | 0.73 | 0.80 |
| BxPC-3 | Pancreas | wt | wt | wt | wt | wt | 4.15 | 0.28 | 0.88 | 0.97 |
| HPAC | Pancreas | wt | wt | mut | wt | wt | 5.01 | 0.20 | 0.92 | 1.59 |
| L3.3 | Pancreas | mut? | wt | mut | wt | wt | 3.43 | 0.44 | 0.86 | 1.3 |
| MIA PaCa-2 | Pancreas | wt | wt | mut | wt | wt | 4.15 | 0.27 | 0.81 | 0.84 |
| PANC-1 | Pancreas | wt | wt | mut | wt | wt | 1.28 | | 0.55 | 0.57 |
| SU.86.86 | Pancreas | wt | wt | mut | wt | wt | 1.85 | 0.59 | 0.79 | 1.18 |
| A549 | Lung | wt | wt | mut | wt | wt | 1.56 | | 0.66 | 0.76 |
| Calu-6 | Lung | wt | wt | mut | wt | wt | 1.97 | | 0.72 | 1.21 |
| NCI-H1792 | Lung | wt | wt | mut | wt | wt | 1.73 | 0.65 | 0.71 | 1.03 |
| NCI-H2030 | Lung | wt | wt | mut | wt | wt | 2.12 | 0.05 | 0.64 | 0.91 |
| NCI-H2122 | Lung | wt | wt | mut | wt | wt | 2.47 | 0.28 | 0.97 | 1.8 |
| (high res.) | | | | | | | 5.49 | 0.29 | 0.98 | |
| NCI-H23 | Lung | wt | wt | mut | wt | wt | 2.12 | 0.20 | 0.65 | 1.28 |
| (high res.) | | | | | | | 3.51 | 0.01 | 0.78 | |
| NCI-H358 | Lung | wt | wt | mut | wt | wt | 3.74 | 0.48 | 0.89 | 1.72 |
| (high res.) | | | | | | | 4.26 | 0.08 | 0.84 | |
| NCI-H441 | Lung | wt | wt | mut | wt | wt | 0.56 | | 0.39 | 0.63 |
| NCI-H460 | Lung | mut? | wt | mut | wt | wt | 3.97 | 0.22 | 0.68 | 0.84 |
| (high res.) | | | | | | | 3.11 | 0.12 | 0.74 | |
| SK-LU-1 | Lung | wt | mut? | mut | wt | wt | 1.13 | | 0.56 | 0.74 |
| COLO 792 | Skin | wt | wt | | wt | wt | 4.89 | 0.24 | 0.98 | 1.92 |
| MeWo | Skin | wt | wt | wt | wt | wt | 2.21 | 0.39 | 0.76 | 0.90 |
| HMCB | Skin | | | wt | mut? | wt | | | 0.53 | 0.62 |
| Hs 944.T | Skin | wt | wt | wt | mut | wt | 1.44 | 0.69 | 0.77 | 0.75 |
| IPC-298 | Skin | wt | wt | wt | mut | wt | 0.55 | 0.84 | 0.85 | 0.92 |
| MEL-JUSO | Skin | wt | wt | wt | mut | wt | 2.11 | 0.68 | 0.86 | 0.92 |
| SK-MEL-2 | Skin | wt | wt | wt | mut | wt | 2.63 | 0.48 | 0.89 | 1.64 |
| SK-MEL-30 | Skin | wt | wt | wt | mut | wt | 0.56 | 1.94 | 0.8 | 1.38 |
| A-375 | Skin | wt | wt | wt | wt | mut | 1.32 | 1.28 | 0.89 | 1.57 |
| COLO 741 | Skin | wt | wt | wt | wt | mut | 1.4 | 0.47 | 0.73 | 0.83 |
| COLO-800 | Skin | wt | wt | wt | wt | mut | 1.43 | 0.94 | 0.97 | 1.65 |

-continued

| Cell Line | Lineage | PIK3CA | PTEN | KRAS | NRAS | BRAF | Synergy Score | Best CI (Inhib = 0.5) | Max. Inhib | Max. GI |
|---|---|---|---|---|---|---|---|---|---|---|
| IGR-1 | Skin | wt | wt | wt | wt | mut | 0.89 | 0.76 | 0.83 | 0.87 |
| LOX IMVI | Skin | wt | wt | wt | wt | mut | 3.19 | | 0.81 | 0.88 |
| IGR-37 | Skin | wt | mut? | wt | wt | mut | 1.42 | 0.95 | 0.77 | 1.45 |
| K029AX | Skin | wt | mut? | wt | wt | mut | 1.09 | 0.90 | 0.91 | 1.15 |
| A2058 | Skin | wt | mut | wt | wt | mut | 0.60 | | 0.63 | 0.89 |
| IGR-39 | Skin | wt | mut | wt | wt | mut | 0.16 | | 0.32 | 0.50 |
| RPMI-7951 | Skin | wt | mut | wt | wt | mut | 0.32 | | 0.45 | 0.66 |
| SK-MEL-24 | Skin | wt | mut | wt | wt | mut | 0.71 | | 0.50 | 1.11 |
| UACC-62 | Skin | wt | mut | wt | wt | mut | 0.97 | 0.87 | 0.81 | 0.89 |
| SK-MEL-31 | Skin | wt | mut | wt | wt | wt | 0.36 | | 0.39 | 0.5 |

Because they should have zero synergy by definition, the scores for drug-with-self dose matrices (run as a control) show the level that is consistent with experimental errors. The standard deviation of drug-with-self synergy scores was ~0.4, so combinations with $S_{Loewe}>1$ can be considered significantly synergistic. Synergistic combinations with dose shifts with $CI_{50}=0.3$ can easily result from minor variations in our data (since the dose matrices have 3× dilutions), so we only consider $CI_{50}<0.3$ to suggest useful dose sparing. Finally, useful combinations need to have substantial inhibition in combination, so we require $I_{max}>0.8$ and consider $GI_{max}>1.5$ to be especially promising.

Figure 2:
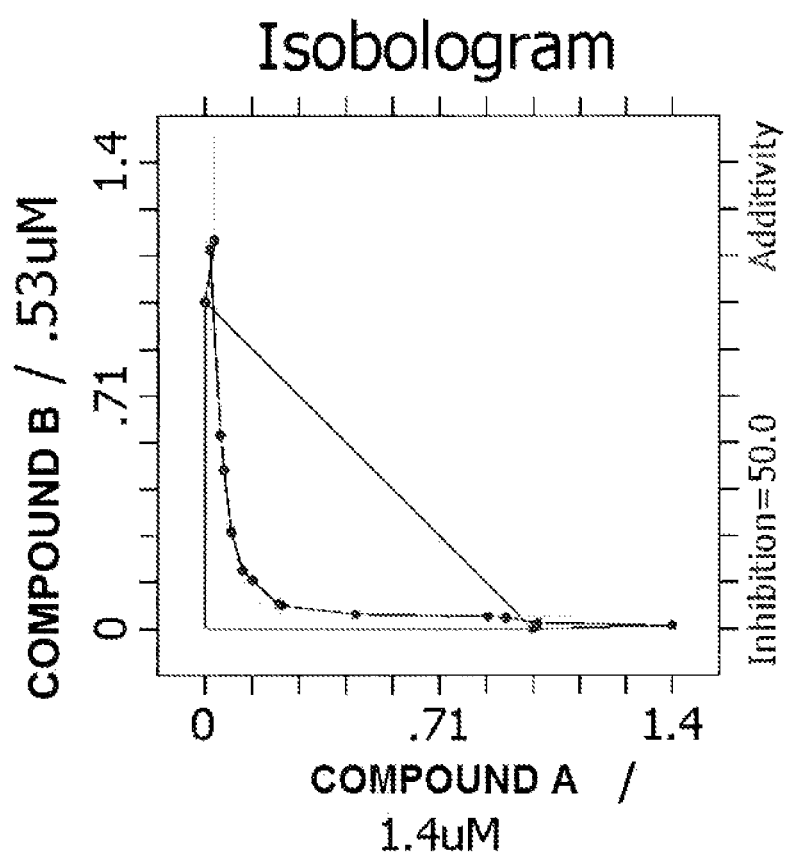
FIG. 2 shows the isobologram contour at 50% inhibition for the combination with (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) and 6-(4-bromo-2-fluorophenylamino)-7-fluoro-3-methyl-3H-benzoimidazole-5-carboxylic acid (2-hydroxyethoxy)-amide (COMPOUND B) in NCI—H2122 non-small cell lung cancer cell lines for high resolution data obtained from a separate study.

Pancreatic Cell Lines:

In pancreatic cell lines, almost all of which are KRAS mutants, the COMPOUND A+COMPOUND B combination was uniformly synergistic, and showed useful dose shifting in four out of seven cases. The best example of synergy is HPAC, which shows strong synergy with a five-fold dose reduction in combination ($CI_{50}=0.2$), and significantly beyond cytostasis ($GI_{max}>1.5$) at the highest concentrations (FIG. 1). Surprisingly, in BxPC-3, the one KRAS wildtype line, the synergy pattern is very similar to that seen in HPAC. The weakest synergy was found for PANC-1, which across the entire dose matrix is never inhibited by more than 50% (FIG. 2)

NSCLC Lung Lines:

In non small-cell lung cancer lines, all of which are KRAS mutants, again the synergy was uniformly strong, with ~5× dose shifting ($CI_{50}\sim0.2$) in most of the cases that had sufficient inhibition levels. (See FIG. 1.) Because, many of the best combination effects showed experimental artifacts in the NSCLC responses, high resolution data from a separate study were also included in the analysis (see FIG. 2), which in all cases confirmed and strengthened the synergy determination.

Melanoma Cell Lines:

Melanoma cell lines showed a variety of interaction types depending on their genetic background (FIG. 3). Synergy was generally found for those with an activating NRAS mutation, and for BRAF mutants. However, these backgrounds showed weak responses to COMPOUND A as a single agent, and the synergy was at much lower levels than were seen for KRAS mutants in pancreatic and lung cancers, and usually confined to very high combined drug concentrations. Strong synergy was seen in COLO 792 and MeWo, both wildtype in Ras, BRAF, and PTEN, but with distinct interaction types due to their very different single agent sensitivities. Synergy was entirely absent for the PTEN mutants, which were resistant to either single agent. Finally, the discrepant cell line LOX IMVI has very different single agent responses to other BRAF mutants, and except for the very highest combined concentrations the interaction looks more like the PTEN mutant combinations.

Overall these results show that there are a variety of interactions that depend on the genetic background of each cell line. In particular, however, KRAS mutants in NSCLC and pancreatic lines tend to show good synergy with useful dose shifting and some emergent cytotoxicity in response to the COMPOUND A+COMPOUND B combination.

The invention claimed is:

1. A method for treating a proliferative disease selected from the group consisting of a colorectal cancer having at least one of a BRAF mutation, KRAS mutation, and PIK3CA mutation and not having a PTEN mutation; a pancreatic cancer having a KRAS mutation; a non-small cell lung cancer having a KRAS mutation; and a melanoma not having a PTEN mutation, comprising the simultaneous, separate or sequential administration of a therapeutically effective amount of the PI3K inhibitor compound (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, in combination with the MEK inhibitor compound 6 (4 bromo-2-fluorophenylamino)-7-fluoro-3-methyl-3H-benzoimidazole-5-carboxylic acid (2-hydroxyethoxy)-amide or a pharmaceutically acceptable salt thereof, to a patient in need thereof having said proliferative disease.

2. A method according to claim 1, wherein the proliferative disease is non-small-cell lung cancer (NSCLC).

* * * * *